United States Patent [19]

Naito et al.

[11] Patent Number: 4,908,444

[45] Date of Patent: Mar. 13, 1990

[54] METHOD OF PRODUCING CEPHEM COMPOUNDS

[75] Inventors: Kenzo Naito, Soraku; Yukio Ishibashi, Suita, both of Japan

[73] Assignee: Takeda Chemical Industries, Ltd., Osaka, Japan

[21] Appl. No.: 3,286

[22] Filed: Jan. 14, 1987

[30] Foreign Application Priority Data

Jan. 23, 1986 [JP] Japan .................................. 61-13186
Dec. 24, 1986 [JP] Japan .................................. 61-310553

[51] Int. Cl.$^4$ .................. C07D 501/04; A61K 31/545
[52] U.S. Cl. ..................................... 540/230; 540/222; 540/228
[58] Field of Search .......................... 540/230, 228, 222

[56] References Cited

U.S. PATENT DOCUMENTS 3,532,694 10/1970 Samefield et al. .................. 540/230
3,728,342  4/1973 Kukolja ............................. 540/230

FOREIGN PATENT DOCUMENTS 0153874 9/1985 European Pat. Off. .
52-27792 3/1977 Japan .
59-46290 3/1984 Japan .

OTHER PUBLICATIONS

Yamana et al, Jour. of Antibiotics vol. XXVII No. 12, p. 1000 (1974).
Heyningen, Jour. of Medicinal Chemistry vol. 10, pp. 22–25 (1965).
Van Heyningen, Journal of Medicinal Chemistry, vol. 8, pp. 22–25 (1965).

*Primary Examiner*—Nicholas S. Rizzo
*Attorney, Agent, or Firm*—Wenderoth, Lind & Ponack

[57] ABSTRACT

A method of producing 3-alkanoyloxymethyl-3-cephem-4-carboxylic acids, which are useful as antibiotics or as intermediates in the synthesis of antibiotics, by reacting a 3-hydroxymethyl-3-cephem-4-carboxylic acid with a saturated fatty acid anhydride in an aqueous medium in the presence of an acid-acceptor base and a 4-(tertiary amino)pyridine.

8 Claims, No Drawings

METHOD OF PRODUCING CEPHEM COMPOUNDS

This invention relates to a method of producing 3-alkanoyloxymethyl-3-cephem-4-carboxylic acids [hereinafter referred to as "acids (II)"], which are useful as antibiotics or as intermediates in the synthesis of antibiotics, in an aqueous medium on a commercial scale and in large quantities using, as starting materials, 3-hydroxy-methyl-3-cephem-4-carboxylic acids [hereinafter referred to as "acids (I)"] on one hand and saturated fatty acid anhydrides on the other.

A method known for the production of acids (II) comprises O-acylation of the 3-hydroxymethyl group of acids (I). However, the O-acylation is carried out under limited reaction conditions since acids (I) are very susceptible to lactonization in acidic solvents [Journal of Medicinal Chemistry, vol. 8, pages 22–25 (1965)]. While the use of readily available and inexpensive saturated fatty acid anhydrides as the O-acylating agents is advantageous for commercial, large-quantity production of acids (II), much remains unknown about the reaction conditions under which said acid anhydrides should be used as O-acylating agents. Specifically, a detour method is known which comprises esterifying the 4-position carboxyl group of acids (I) for the purpose of preventing lactonization, then performing O-acylation and finally conducting deesterification to give acids (II) [U.S. Pat. No. 3,532,694]. Further, methods are known for O-acylation in an anhydrous organic solvent in the presence of a base. Thus, acids (I) are reacted with acid anhydrides in the presence of a tertiary amine having a pKa value of not less than 8 to give acids (II) [Publication of Unexamined Japanese Patent Application No. 27792/77] or acids (I) are reacted with activated acylating agents derived from acids having a pKa value of less than 4.75 in a nonpolar liquid solvent in the presence of a 4-(tertiary amino)pyridine catalyst and an acid-acceptor base to give acids (II) [EP-153874A]. According to a further method known for O-acylation in the presence of a special compound, acids (I) are reacted with acyl derivatives in an inactive solvent, in the presence of 5-mercapto-1,2,3-triazole or a metal salt thereof to give acids (II) [Publication of Unexamined Japanese Patent Application No. 46290/84].

For commercial, large-quantity production of acids (II) by O-acylation of acids (I), it would be advantageous if the production of starting acids (I) could be followed by the production of acids (II) without need of isolating acids (I). Meanwhile, the starting acids (I) are generally produced either by acylating the 7-position amino group of the corresponding 7-amino-3-hydroxymethyl-3-cephem-4-carboxylic acids or by introducing a protective group into the amino group at position 7 or in a 7-position acyl group of the corresponding 7-amino or acylamino-3-hydroxymethyl-3-cephem-4-carboxylic acids. The 7-position acylation and protective group introduction reactions in the production of said acids (I) are generally carried out in an aqueous medium. Therefore, for the production of the desired acids (II) from the starting acids (I) as produced without isolation thereof, the O-acylation of acids (I) for the production of acids (II) should necessarily be carried out in the same aqueous solvent. According to the known methods of producing acids (II) by O-acylating acids (I), however, the O-acylation should preferably be carried out generally in an anhydrous organic solvent. As an exception, there is known the method for the production of acids (II) by O-acylation of acids (I) in an inactive solvent to which water is added for promoting the reaction, in the presence of the specific compound, i.e. 5-mercapto-1,2,3-triazole or a metal salt thereof, but the used specific compound is an expensive reagent and is required in large amounts in the method. Therefore, said method is not advantageous to large-quantity commercial production of acids (II). Thus, the prior art methods do not suggest any advantageous conditions to be employed, using the acids (I) in a reaction mixture form as produced by the reaction in an aqueous medium as the starting materials, for commercial, large-quantity production of acids (II) by O-acylation of acids (I) in an aqueous medium. Furthermore, the prior art methods do not suggest any conditions to be employed for the prevention of lactonization of acids (I) in aqueous media which is essential in commercial production of acids (II) without isolation of acids (I) or any reaction conditions suited for producing acids (II) in high yield using saturated fatty acid anhydrides as the O-acylating agents.

As a result of their investigations, the present inventors unexpectedly found that the reaction of acids (I) with saturated fatty acid anhydrides, when effected in an aqueous medium in the presence of an acid-acceptor base and a 4-(tertiary amino)pyridine, (i) does not lead to lactonization of acids (I) at all;

(ii) can lead to O-acylation of acids (I) in said aqueous medium;

(iii) allows the saturated fatty acid anhydrides to serve as O-acylating agents;

(iv) allows the acids (I) to be amphoteric substances insoluble in anhydrous organic solvents; and (v) gives the desired acids (II) in high yields.

On the basis of these findings, the present inventors have now completed the present invention which is concerned with a commercially advantageous method of producing acids (II).

Thus, the invention provides a method of producing acids (II) which comprises reacting acids (I) with saturated fatty acid anhydrides in an aqueous medium in the presence of an acid-acceptor base and a 4-(tertiary amino)pyridine.

Accordingly, in a method of producing acids (II) by O-acylation of acids (I) with saturated fatty acid anhydrides, the invention has made it possible to produce acids (II) in high yields in the same aqueous solvent systems as used in the production of acids (I). As a result, according to the invention acids (II) can be produced advantageously in commercial, large-quantity production from acid (I) without isolation thereof.

The starting acids (I) to be used in accordance with the invention are 3-cephem compounds having a hydroxymethyl group at position 3 and a carboxyl group at position 4, or salts thereof. Thus, for instance, acids (I) obtained by fermentative production or acids (I) derived therefrom by chemical or enzymatic treatment are generally used as the starting materials in the practice of the invention.

Preferred examples of acids (I) are compounds of the formula

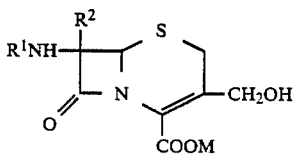

(IA)

wherein $R^1$ is a hydrogen atom, amino-protective group or an acyl group, $R^2$ is hydrogen atom, methoxy group or formylamino group and M is a hydrogen atom or a salt-forming atom or group. In formula (IA), $R^1$ represents a hydrogen atom and an acyl group derived from a carboxylic acid. The acyl group of $R^1$ includes phenylacetyl, phenoxyacetyl and 5-amino-5-carboxyvaleryl with or without a protective group on the amino or carboxyl group, and further those acyl groups which are generally employed as substituents in position 6 of penicillin derivatives or in position 7 of cephalosporin derivatives, for example aliphatic carboxylic acid-derived acyl groups such as formyl, acetyl, propionyl, hexanoyl, butanoyl, heptanoyl, octanoyl and cyclopentanecarbonyl, substituted aliphatic carboxylic acid-derived acyl groups (whose amino and/or carboxyl group, if any, may be protected) such as 2-thienylacetyl, tetrazolylthioacetyl, tetrazolylacetyl, cyanoacetyl, acetoacetyl, 4-methylthio-3-oxobutyryl, 4-carbamoylmethyl -thio-3-oxobutyryl, α-phenoxypropionyl, α-phenoxybutyryl, p-nitrophenylacetyl, (2-pyridyloxy)acetyl, (3-pyridyloxy)acetyl, (4-pyridyloxy)acetyl, (2-oxothiazolin-4-yl)acetyl, (2-aminothiazol-4-yl)acetyl, 4-pyridylthioacetyl, (3-sydonon)acetyl, 1-pyrazolylacetyl, 2-furylacetyl, (2-oxo-3-methylpyridazin-6-yl)thioacetyl, α-carboxyphenylacetyl, α-aminophenylacetyl, mandelyl, α-sulfophenylacetyl, α-sulfo-(p-aminophenyl)acetyl, phenylglycyl, 1-cyclohexenylglycyl, thienylglycyl, furylglycyl, cyclohexadienylglycyl, α-(β-methylsulfonylethoxycarbonyl)aminophenylacetyl, 2-(2-amino-4-thiazolyl)-2-methoxyiminoacetyl, 2-(2-amino-4thiazolyl) -2-[(1-methyl-1-carboxyethyl)oxyimino]acetyl and 2-(2-amino-4-thiazolyl)-2-carboxymethyloxyiminoacetyl, aromatic acyl groups such as benzoyl and p-nitrobenzoyl, and heterocyclecarbonyl groups such as 5-methyl-3-phenyl-4-isoxazolylcarbonyl and 3-(2,6-dichlorophenyl)-5-methyl-4-isoxazolylcarbonyl. $R^2$ is, for example, a hydrogen atom, xethoxy group or formylamino group. The salt forming atom or group represented by M may be preferably an alkali metal such as lithium, sodium or potassium, an alkaline earth metal such as calcium or magnesium, or an ammonium group derived from such an amine as dicyclohexylamine, triethylamine, tributylamine, diethylamine or trimethylamine.

Particularly preferred acids (I) are amphoteric substances insoluble in anhydrous organic solvents, for example compounds of the formula

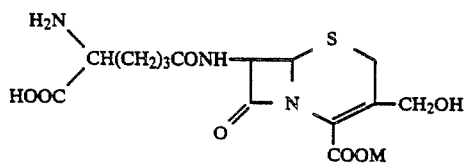

(IB)

wherein M is as defined above. A typical example of such amphoteric substances (IB) is desacetylcephalosporin C which is producible fermentatively in high concentrations or obtainable as a byproduct in fermentative production of cephalosporin C. Desacetylcephalosporin C is generally subjected to amino-protective group introduction reaction in water or a mixture of water and an organic solvent under basic conditions. In accordance with the invention, the reaction mixture obtained after said protective group introduction reaction can be used as it is as the starting material. [According to the prior art methods, the reaction mixture obtained after said protective group introduction reaction is acidified and the product is then isolated, dehydrated or dried, and used as the starting material. Accordingly, lactonization occurs under acidic conditions, whereby the yield of the starting material is reduced.]

Referring to the above (I), (IA) and (IB), the amino group in position 7 [e.g. in case where $R^1$=H in formula (IA)] or the amino and/or carboxyl group on the acyl group in position 7 and/or the like functional group or groups each may be protected by an appropriate protective group in the conventional method. Thus, for example, aromatic acyl groups such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, aliphatic acyl groups such as acetyl, valeryl, caprylyl, n-decanoyl, acryloyl, pivaloyl, camphorsulfonyl, methanesulfonyl and chloroacetyl, esterified carboxyl groups such as ethoxycarbonyl, isobornyloxycarbonyl, phenoxycarbonyl, trichloroethoxycarbonyl and benzyloxycarbonyl, carbamoyl groups such as methylcarbamoyl, phenylcarbamoyl and naphthylcarbamoyl, and similar thiocarbamoyl groups may be used as aminoprotective groups. And, the protective group for carboxyl group includes any group which can be conventionally used as a carboxyl-protective group in the field of β-lactam and peptide, such as benzyl, p-nitrobenzyl, tert-butyl, trityl and 2-trimethylsilylethyl.

Used as the saturated fatty acid anhydrides are, for instance, compounds of the formula

(III)

wherein $R^3$ is an alkyl group. The group $R^3$ in formula (III) may be an alkyl group containing 1–8 carbon atoms, such as methyl, ethyl, propyl, butyl, pentyl or hexyl.

Preferred acid anhydrides (III) are acetic anhydride (pKa=4.75) and propionic anhydride (pKa=4.87), among others.

The aqueous medium may be, for example, water or a mixture of water and an organic solvent. Said organic solvent includes, among others, ethers such as dioxane and tetrahydrofuran, amides such as formamide, N,N-dimethylformamide and N,N-dimethylacetamide, nitriles such as acetonitrile, halogenated hydrocarbons such as dichloromethane and chloroform, and ketones such as acetone. The amount of water in the water-organic solvent mixture is generally 0.01–10 volume parts, preferably 0.1–5 volume parts, more preferably 0.2–1 volume part, per volume part of the organic solvent used. The mixed solvent is used in an amount such that the mole ratio of water to the used saturated fatty acid anhydride should amount to generally 2–100:1, preferably 3–50:1, more preferably 20–30:1.

Mixtures of water and tetrahydrofuran in the above volume ratios, for instance, are preferable aqueous medium. And, when the compounds (IB) whose amino and/or carboxyl group in the 7-acyl group may be protected are used as the starting material, water may be preferably used as the aqueous medium. The acid acceptor base may be a base which neutralizes the byproduct acid resulting from the O-acylation reaction in this invention to thereby promote said reaction. Examples of such base are tri-$C_{1-6}$alkylamine such as triethylamine, trimethylamine and tributylamine, and cyclic tertiary amines such as N-methylpyrrolidine, N-methylpiperidine, pyridine, α-picoline, β-picoline, γ-picoline, 2,6-lutidine, 1,5-diazabicyclo[4.30]non-5-ene and 1,8-diazabicyclo[5.4.0]undec-7-ene.

Tri-$C_{1-3}$ alkylamines such as triethylamine, for instance, may be preferable acid acceptor bases.

The 4-(tertiary amino)pyridine may be a pyridine substituted at position 4 by a tertiary amino group. Examples of such pyridine are compounds of the formula

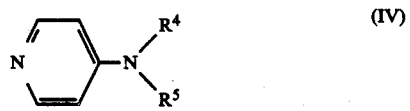

(IV)

wherein $R^4$ and $R^5$ are the same or different and each is an alkyl group or $R^4$ and $R^5$ combinedly together with the adjacent nitrogen atom represent a cyclic amino. The alkyl group represented by each of $R^4$ and $R^5$ in formula (IV) is, for example, a lower alkyl group containing 1–6 carbon atoms, such as methyl, ethyl, propyl, isopropyl or butyl. The cyclic amino represented by $R^4$ and $R^5$ together with the adjacent nitrogen atom is, for example, a cyclic tertiary amino such as piperidino, 4-methylpiperidino or pyrrolidino. Concrete examples of the pyridine (IV) are 4-(dimethylamino)pyridine, 4-(diethylamino)pyridine, 4-(di-n-propylamino)pyridine, 4-(diisopropylamino)pyridine, 4-(N-methyl-N-ethylamino)pyridine, 4-(N-ethyl-N-propylamino)pyridine, 4-pyrrolidinopyridine, 4-(4-methylpyrrolidino)pyridine and 4-piperidinopyridine. These 4-(tertiary amino)pyridines can be recovered after the reaction in this invention and can be reused.

4-(Di-$C_{1-3}$ alkylamino)pyridines such as 4-(dimethylamino)pyridine may be preferable 4-(tertiary amino)pyridines. The desired product acids (II) are 3-cephem compounds having an alkanoyloxymethyl group in position 3 and a carboxyl group in position 4, or salts thereof. When the above acids (IA) and saturated fatty acid anhydrides (III) are used as the starting materials, acids of the formula

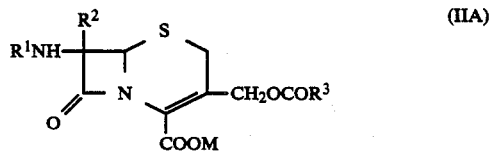

(IIA)

wherein $R^1$, $R^2$, $R^3$ are as defined above, are obtained as the products of the method according to the invention. When the acids (IB) and saturated fatty acid anhydrides (III) are used as the starting materials, the products are acids of the formula

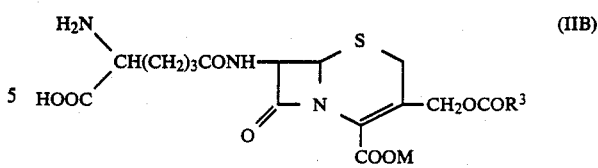

(IIB)

wherein $R^3$ and M are as defined above. Referring to (II), (IIA) and (IIB), the 7-position amino group [e.g. in case where $R^1$=H in formula (IIA)] or the amino and/or carboxyl group and/or other functional group or groups in the 7-position acyl group may optionally be protected as in the case of (I),(IA) and (IB).

In accordance with the invention, the acids (I) are reacted with the saturated fatty acid anhydrides in the aqueous solvent in the presence of the acid acceptor base and the 4-(tertiary amino)pyridine.

The saturated fatty acid anhydrides may be generally used in an amount of 1–10 moles per mole of acids (I). When hydrolysis of the saturated fatty acid anhydrides is anticipated, it is recommendable to use the saturated fatty acid anhydrides in an amount of not less than 2 moles (preferably 2–6 moles) per mole of acids (I). The reaction is carried out in the aqueous medium in the presence of the acid acceptor base and 4-(tertiary amino)pyridine. The most preferred mode of practice comprises adding the saturated fatty acid anhydride to the aqueous medium containing-the acid (I), acid acceptor base and 4-(tertiary amino)pyridine. The acid acceptor base may be used generally in an amount of 1–10 moles, preferably 1–6 moles, more preferably 1–3 moles, per mole of the saturated fatty acid anhydride. The 4-(tertiary amino)pyridine can promote the reaction in a catalytic amount and may generally be used in an amount of 0.001–1 mole, preferably not more than 0.02 mole (specifically 0.001–0.02 mole), per mole of the saturated fatty acid anhydride. The amount of the aqueous medium is not critical provided that it does not interfere wit the reaction, and can suitably be selected depending on the kind and amount each of acid (I), saturated fatty acid anhydride and medium. The reaction temperature may generally lie within the range of −30° C. to 40° C., preferably within the range of −20° C. to 20° C. The reaction period depends to some extent on the reaction temperature. Generally, however, the reaction may be complete in a short time. For example, when the reaction is carried out at about 10° C., the reactionmay generally be complete in 0.5–1.5 hours. The acids (II) thus produced may be isolated and purified by known means, such as concentration, concentration under reduced pressure, solvent extraction, pH adjustment, phase transfer, crystallization, recrystallization, chromatography and combinations of these.

The thus-obtained acids (II), when in the free acid state (M=H), may be converted, as necessary, to appropriate salts or esters (inclusive of pharmacologically acceptable salts or esters) by conventional methods or, when in a salt form (M=salt-forming group), may be converted to the free form relative to the 4-position carboxyl group by a conventional method. The acids (II) in salt or free form may be converted to other appropriate salts or various esters. The acids (II) in such free, salt or ester form may be used either as antimicrobial agents or as starting materials for the production of more potent antimicrobial agents.

The starting acids (I) to be used in the invention can be produced, for example, by fermentative methods [e.g. methods described in Nature, vol. 246, page 154 (1973), U.S. Pat. No. 3,926,729, etc.] or by chemical or enzymatic treatment of the fermentation products [e.g. methods described in Biochemical Journal, vol. 81, pages 591-596 (1961), etc.].

The product acids (II) can be used as they are as antibiotics having excellent antimicrobial activity abcording to the prior art teachings [e.g. methods described in British Patents Nos. 1445979, 1580621 and 1580623, U.S. Pat. Nos. 3,926,957, 3,936,443, 4,024,133, 4,033,950 and 4,093,803, etc.] and also as intermediates in the synthesis of antibiotics having improved antimicrobial activity. For example, the acids (II) can be converted to the corresponding 7-[2-(2-imino-4-thiazolin-4-yl)acetamido] derivatives by cleavage of the 7-position acyl group by a per se known method [e.g. methods described in U.S. Pat. Nos. 3,697,515, 3,499,909, 3,882,108 and 3,632,578, etc.], reaction with 4-halo-3-oxobutyryl halide and further reaction of the resulting 4-halo-3-oxobutyrylamides with thiourea [as described in U.S. Pat. No. 4,080,498, etc.]. Said derivatives generally have good antimicrobial activity, although they differ more or less in such activity depending on the kind of the 3-position substituent.

The following examples illustrate the invention in more detail but are by no means limitative of the scope of the invention.

In the examples and reference examples, the following abbreviations are used:

s for singlet, br for broad, d for doublet, dd for double doublet, t for triplet, q for quartet, ABq for AB pattern quartet, m for multiplet, D$_2$O for deuterated water, % for percent by weight, DMSO-d$_6$ for dimethyl sulfoxide-d$_6$.NMR (nuclear magnetic resonance) spectra were measured, unless otherwise specified, at 90 MHz with tetramethylsilane as an internal standard and the chemical shift values are given in terms of δ values (ppm).

EXAMPLE 1

7-(D-5-Carboxy-5-phthalimidovaleramido)-3-hydroxy methyl-3-cephem-4-carboxylic acid ditriethylamine salt (5.69 g), 4-(dimethylamino)pyridine (50 mg) and triethylamine (7.0 ml) were dissolved in aqueous tetrahydrofuran (tetrahydrofuran 20 ml-water 3 ml). Acetic anhydride (4.7 ml) was added dropwise to the solution with ice cooling over 25 minutes. The resultant mixture was stirred with ice cooling for 30 minutes. Thereafter, the reaction mixture was diluted with water, adjusted to pH 1.5 with concentrated hydrochloric acid and extracted with methylene chloride-tetrahydrofuran (2:1 by volume). The organic layer was concentrated to dryness. The residue was again dissolved in aqueous tetrahydrofuran, the solution was adjusted to pH 6.5 with 2 N sodium hydroxide aqueous solution, the office solvent was distilled off under reduced pressure and the residue was lyophilized to give 4.24 g of 3-acetoxymethyl- 7-(D-5-carboxy-5-phthalimidovaleramido)-3-cephem-4-carboxylic acid disodium salt. Yield 89.2%.

NMR (D$_2$O): δ 7.77 (4H, br s), 5.50 (1H, d, J=5 Hz), 4.96 (1H, d, J=5 Hz), 4.89 and 4.63 (2H, ABq, J=12 Hz), 3.45 and 2.97 (2H, ABq, J=18 Hz), 2.36 (2H, m), 2.10 (3H, s), 1.65 (4H, m)

EXAMPLE 2

7-(D-5-Carboxy-5-phenoxycarbonylaminovaleramido)-3-hydroxymethyl-3-cephem-4-carboxylic acid disodium salt (4.92 g), sodium chloride (2.0 g), 4-(dimethylamino)pyridine (50 mg) and triethylamine (8.4 ml) were dissolved in tetrahydrofuran 20 ml-water 10 ml. The solution was cooled to −20° C. and acetic anhydride (4.7 ml) was added thereto. Then the temperature was raised to 5° C., and the mixture was stirred at that temperature for 30 minutes, then diluted with water, adjusted to pH 2.0 by addition of concentrated hydrochloric acid and extracted with methylene chloride-tetrahydrofuran (2:1 by volume). The organic layer was cooled in a dry ice bath and the resultant precipitate ice was removed by filtration. The filtrate was concentrated to dryness. The residue was dissolved in aqueous acetonitrile (acetonitrile 30 ml-water 15 ml). The solution was adjusted to pH 5.5 by addition of 20% sodium hydroxide aqueous solution, then purified by column chromatography using Amberlite XAD-II (Rohm and Haas), and adjusted to pH 2.0 by addition of 1N hydrochloric acid. The resultant precipitate was collected and lyophilized to give 4.08 g of 3-acetoxymethyl-7-(D-5-carboxy-5-phenoxycarbonylamino valeramido)-3-cephem-4-carboxylic acid as a powder. Yield 83.2%.

NMR (DMSO-d$_6$): δ 8.70 (1H, d, J=8 Hz), 7.94 (1H, d, J=8 Hz), 7.45–6.95 (5H, m), 5.65 (1H, dd, J=5 and 8 Hz), 5.04 (1H, d, J=5 Hz), 4.97 and 4.65 (2H, ABq, J=12 Hz), 4.0 (1H, m), 3.63 and 3.37 (2H, ABq, J=18 Hz), 2.2 (2H, m), 2.01 (3H, s), 1.7 (4H, m)

EXAMPLE 3

7-(D-5-Aminoadipamido)-3-hydroxymethyl-3-cephem-4-carboxylic acid sodium salt (19.77 g) was dissolved in water 50 ml-tetrahydrofuran 25 ml. Phenyl chloroformate (8.6 g) was added dropwise to the solution with ice cooling over 15 minutes while the pH of the solution was adjusted to and maintained at 9.3±0.2 ition of 20% sodium hydroxide aqueous solution. Thereafter the mixturee was stirred with ice cooling for 10 minutes to complete the reaction. Assay by high-performance liquid chromatography showed that the reaction mixture contained 22.50 g (yield 91.2%) of 7-(D-5-carboxy-5-phenoxycarbonylaminovaleramido)-3-hydroxymethyl-3-cephem-4-carboxylic acid. In the thus-obtained solution were dissolved sodium chloride (5.0 g), 4-(dimethylamino)pyridine (0.25 g), triethylamine (42.0 ml) and tetrahydrofuran (75 ml). The solution was cooled to −20° C. Thereto was added acetic anhydride (23.5 ml), and the mixture was stirred with ice cooling for 30 minutes. Thereafter the reaction mixture was diluted with water and extracted with methylene chloride-tetrahydrofuran (2:1 by volume). The organic layer was cooled in a dry ice bath, the precipitate ice was removed by filtration and the filtrate was concentrated to dryness. To the residue was added methylene chloride (400 ml) and triethylamine (15.4 ml) for dissolution of the residue. Assay by high-performance liquid chromatography revealed that this solution contained 22.07 g (yield 90.4%) of 3-acetoxymethyl-5-phenoxycarbonylaminovaleramido)-3-cephem-4-carboxylic acid.

EXAMPLE 4

7-(D-5-Carboxy-5-phenoxycarbonylaminovaleramido)-3-hydroxymethyl-3-cephem-4- carboxylic acid ditriethylamine salt (2.04 g), 4-(dimethylamino)pyridine (15 mg) and triethylamine (2.1 ml) were dissolved in tetrahydrofuran 6 ml-water 0.9 ml. To the solution was added dropwise with ice cooling over 15 minutes propionic anhydride (1.93 ml), and the mixture was stirred with ice cooling for 30 minutes. Thereafter the reaction mixture was diluted with water, adjusted to pH 1.5 with concentrated hydrochloric acid and extracted with methylene chloride-tetrahydrofuran (2:1 by volume). Water was added to the organic layer and the pH was adjusted to 6.5 by addition of 2N sodium hydroxide. The aqueous layer was separated and lyophilized to give 1.46 g of 7-(D-5-carboxy-5-phenoxycarbonylvaleramido)-3-propionyloxymethyl-3-cephem-4-carboxylic acid disodium salt. Yield 83.9%.

NMR ($D_2O$): $\delta$ 7.5–7.0 (5H, m), 5.56 (1H, d, J=5 Hz), 5.04 (1H, d, J=5 Hz), 4.85 and 4.63 (2H, ABq, J=13 Hz), 4.0 (1H, m), 3.59 and 3.23 (2H, ABq, J=18 Hz), 2.35 (2H, q, J=7 Hz), 2.4 (2H, m), 1.8 (4H, m), 1.06 (3H, t, J=7 Hz)

EXAMPLE 5

7-(D-5-Aminoadipamido)-3-hydroxymethyl-3-cephem-4-carboxylic acid sodium salt (19.77 g) was dissolved in water 100 ml-tetrahydrofuran 50 ml. Ethyl chloroformate (5.23 ml) was added dropwise with ice cooling over 20 minutes while the pH of the reaction mixture was adjusted to 9.3±0.2 with 20% sodium hydroxide. After stirring with ice cooling for further 15 minutes, the organic solvent was distilled off under reduced pressure, the remaining solution was adjusted to pH 1.5 by addition of concentrated hydrochloric acid, and the resultant precipitate was collected by filtration and washed with water to give 15.6 g of 7-(D-5-carboxy-5-ethoxycarbonyl -aminovaleramido)-3-hydroxymethyl-3-cephem-4-carboxylic acid as a white powder. The whole amount of the powder obtained, 4-(dimethylamino)pyridine (0.25 g) and triethylamine (50.4 ml) were dissolved in tetrahydrofuran 100 ml-water 15 ml. Acetic anhydride (23.5 ml) was added dropwise to the solution with ice cooling over 25 minutes and the resultant mixture was stirred with ice cooling for 30 minutes. Thereafter the reaction mixture was diluted with water and adjusted to pH 1.5 with concentrated hydrochloric acid. After addition of sodium chloride for salting out, the mixture was extracted with tetrahydrofuran. The organic layer was concentrated, the residue was suspended in water, and the suspension was adjusted to pH 6.5 by addition of 20% sodium hydroxide aqueous solution and lyophilized to give 14.9 g of 3-acetoxymethyl-7-(D-5-carboxy-5-ethoxycarbonylaminovaleramido)-3-cephem-4carboxylic acid disodium salt. The yield from 7-(D-5-aminoadipamido)-3-hydroxymethyl-3-cephem-4-carboxylic acid sodium salt was 56.1% and the yield in the acetylation step was 80.1%.

NMR ($D_2O$): $\delta$ 5.56 (1H, d, J=5 Hz), 5.05 (1H, d, J=5 Hz), 4.86 and 4.65 (2H, ABq, J=12 Hz), 4.04 (2H, q, J=7 Hz), 3.9 (1H, m), 3.64 and 3.32 (2H, ABq, J=18 Hz), 2.35 (2H, m), 2.07 (3H, s), 1.7 (4H, m), 1.20 (3H, t, J=7 Hz)

EXAMPLE 6

7-(D-5-Aminoadipamido)-3-hydroxymethyl-3-cephem-4-carboxylic acid sodium salt (3.95 g) was dissolved in water 20 ml-tetrahydrofuran 10 ml. Benzoyl chloride (1.28 ml) was added dropwise to the solution with ice cooling over 10 minutes while the reaction mixture was adjusted to pH 9.3±0.2 with 20% sodium hydroxide aqueous solution. The resultant mixture was stirred with ice cooling for 20 minutes, the organic solvent was then distilled off, the remaining solution was adjusted to pH 2.0 by addition of concentrated hydrochloric acid, sodium chloride was added for salting out, and the whole mixture was extracted with tetrahydrofuran. Triethylamine (3.1 ml) was added to the organic layer and the mixture was concentrated to dryness to give 5.20 g of 7-(D-5-benzamido -5-carboxyvaleramido)-3-hydroxymethyl-3-cephem-4-carboxylic acid ditriethylamine salt. The whole amount of the substance obtained, 4-(dimethylamino)pyridine (50 mg) and triethylamine (7.0 ml) were dissolved in tetrahydrofuran 20 ml-water 3 ml. Acetic anhydride (4.7 ml) was added dropwise to the solution over 15 minutes with ice cooling and the resultant mixture was stirred with ice cooling for further 30 minutes. Thereafter the reaction mixture was diluted with water, adjusted to pH 1.5 with concentrated hydrochloric acid and extracted with methylene chloride-tetrahydrofuran (2:1 by volume). The organic layer was concentrated to dryness, the residue was dissolved again in water 30 ml-tetrahydrofuran 30 ml. The solution was adjusted to pH 6.5 with 2N sodium hydroxide aqreous solution, concentrated and to give 3.48 g of 3-acetoxymethyl-7-(D-5-benzamido-5-carboxyvaleramido)-3-cephem-4-carboxylic acid disodium salt. The yield from 7-(D-5-aminoadipamido)-3-hydroxy methyl-3-cephem-4-carboxylic acid sodium salt was 61.8% and the acetylation yield was 80.7%.

NMR ($D_2O$): $\delta$7.8–7.4 (5H, m), 5.54 (1H, d, J=5 Hz), 5.01 (1H, d, J=5 Hz), 4.84 and 4.61 (2H, ABq, J=12 Hz), 3.52 and 3.09 (2H, ABq, J=18 Hz), 2.4 (2H, m), 2.08 (3H, s), 1.8 (4H, m)

EXAMPLE 7

7-(D-5-Carboxy-5-phenoxycarbonylaminovaleramido)-3-hydroxymethyl-3-cephem-4-carboxylic acid disodium salt (5.21 g), sodium chloride (2.0 g), 4-(dimethylamino)pyridine (50 mg) and triethylamine (8.4 ml) were dissolved in water (10 ml). The solution was cooled to −15° C. and, after addition of acetic anhydride (4.7 ml), warmed to 5° C. and stirred at that temperature for 30 minutes. The reaction mixture was diluted with water, adjusted to pH 2.0 by addition of concentrated hydrochloric acid and extracted with a mixed solvent composed of methylene chloride and tetrahydrofuran (2:1 by volume). The organic layer was cooled in a dry ice bath, the precipitate ice was removed by filtration and the filtrate was concentrated to dryness. The residue was dissolved in aqueous acetonitrile (acetonitrile 25 ml-water 25 ml) and assayed by high-performance liquid chromatography. It was shown that the solution contained 4.21 g of 3-acetoxymethyl-7-(D-5-carboxy-5-phenoxycarbonylaminovaleramido)-3-cephem-4-carboxylic acid. Yield 81.1%.

EXAMPLE 8

7-[2-(2-Chloroacetamidothiazol-4-yl)-(Z)-2-methoxyiminoacetamido]-3-hydroxymethyl-3-cephem-4-carboxylic acid sodium salt (1.54 g), 4-(dimethylamino)-pyridine (15 mg) and triethylamine (2.5 ml) were dissolved in a mixed solvent composed of tetrahydrofuran (5 ml) and water (1ml). The solution was cooled to −15° C. and propionic anhydride (1.9 ml) was added to the solution and the mixture was warmed to 10° C. and stirred at that temperature for 1 hour. The reaction mixture was then diluted with water, adjusted to pH 2.0 by addition of concentrated hydrochloric acid and extracted with a mixed solvent composed of methylene chloride and tetrahydrofuran (2:1 by volume). The organic layer was cooled in a dry ice bath, the precipitate ice was removed by filtration and the filtrate was concentrated to dryness. Diethyl ether (30 ml) was added to the residue, the resultant suspension was filtered and the solids were dried under reduced pressure to give 1.51 g of 7-[2-(2-chloroacetamidothiazol-4-yl)-(Z)-2-methoxyiminoacetamido]-3-propionyloxymethyl-3-cephem-4-carboxylic acid as a NMR (DMSO-$d_6$): δ 9.60 (1H, d, J=8 Hz, CONH), 7.40 (1H, s, thiazole $C_5$), 5.81 (1H, dd, J=5 and 8 Hz, $C_7$), 5.15 (1H, d, J=5 Hz, $C_6$), 5.02 and 4.69 (2H, ABq, J=13 Hz, $C_3$—$CH_2$), 4.36 (2H, s, $ClCH_2CO$), 3.88 (3H, s, $OCH_3$), 3.67 and 3.43 (2H, ABq, J=18 Hz, $C_2$), 2.34 (2H, q, J=7 Hz, $\underline{CH_2}CH_3$), 1.04 (3H, t, J=7 Hz, $CH_2\underline{CH_3}$)

EXAMPLE 9

7-(D-5-Aminoadipamido)-3-hydroxymethyl-3-cephem-4-carboxylic acid sodium salt (49.4 g) was dissolved in water (125 ml). Ethyl chloroformate (13.1 ml) was added dropwise with ice cooling over 20 minutes while the pH of the reaction mixture was adjusted to 8.9±0.1 with 20% sodium hydroxide aqueous solution (41.9 ml). After stirring with ice cooling for further 20 minutes, the reaction mixture was assayed by high-performance liquid chromatography. The assay showed that the reaction mixture contained at the most 57.2 g of 7-(D-5-carboxy-5-ethoxycarbonylaminovaleramido)-3-hydroxymethyl-3-cephem-4-carboxylic acid sodium salt, since 1.0 g of 7-(D-5-aminoadipamido)-3-hydroxymethyl-3-cephem-4-carboxylic acid sodium salt was contained therein. The reaction mixture was cooled to −5° C., and triethylamine (52.5 ml) and 4-(dimethylamino)pyridine (0.15 g) were added thereto. {The mixture was cooled to −10° C. and, after addition of acetic anhydride (23.5 ml) over 20 minutes, warmed to room temperature (20° C.) and stirred for 30 minutes. Thereafter the resultant mixture was diluted with water (250 ml) and tetrahydrofuran (125 ml) and, after addition of sodium chloride (110 g), was adjusted to pH 1.8 with concentrated hydrochloric acid (53 ml). The mixture was extracted with methylene chloride (250 ml), and the aqueous layer was extracted twice with tetrahydrofuran (62.5 ml). The combined organic layer was concentrated under reduced pressure, the precipitated powder was suspended in methylene chloride (400 ml), collected by filtration, washed with methylene chloride (125 ml) and then dried under reduced pressure to give 58.5 g of 3-acetoxymethyl-7-(D-5-ethoxycarbonylaminovaleramido)-3-cephem-4-carboxylic acid as a white powder. The yield from 7-(D-5-carboxy-5-ethoxycarbonylaminovaleramido)-3-hydroxymethyl-3-cephem-4-carboxylic acid sodium salt was 98.0%.

NMR (DMSO-$d_6$): δ 8.66 (1H, d, J=8 Hz), 7.21 (1H, d, J=8Hz), 5.60 (1H, dd, J=5 and 8 Hz), 5.02 (1H, d, J=5Hz), 4.96 and 4.64 (2H, ABq, J=13 Hz), 3.95 (2H, q, J=7 Hz), 4.0–3.7 (1H, m), 3.64 and 3.38 (2H, ABq, J=18 Hz), 2.3–2.0 (2H, m), 2.00 (3H, S), 1.8–1.4 (4H, m), 1.15 (3H, t, J=7 Hz)

EXAMPLE 10

7-(D-5-Aminoadipamido)-3-hydroxymethyl carboxylic acid sodium salt (11.9 g) and 4-(dimethylamino)pyridine (0.11 g) were dissolved in water (30 ml). The solution was cooled to 0° C. and triethylamine (30 ml) was added to the solution. The mixture was cooled to −10° C. and, after addition of acetic anhydride (14.1 ml) over 10 minutes, warmed to room temperature (20° C.) and stirred for 30 minutes. Thereafter the reaction mixture was diluted with water (60 ml) and adjusted to pH 2.0 with concentrated hydrochloric acid (21.5 ml) with ice cooling. After addition of sodium chloride (24 g) for salting out, the mixture was extracted three times with tetrahydrofuran (40 ml). The combined organic layer was concentrated to dryness and the residue was dissolved in methylene chloride 60 ml - triethylamine 8.4 ml. The solution was added dropwise to diethyl ether (600 ml), and the precipitated powder was collected by filtration and dried under reduced pressure to give 16.4 g of 7-(D-5-acetamido-5-carboxyvaleramido)-3-acetoxymethyl-3-cephem-4-carboxylic acid ditriethylamine salt. Yield 82.6%.

NMR (CDCl$_3$): δ 7.57 (1H, d, J=8 Hz), 6.80 (1H, d, J=7 Hz) 5.65 (1H, dd, J=5 and 8 Hz), 4.91 (1H, d, J=5 Hz), 5.06 and 4.82 (2H, ABq, J=12 Hz), 4.5–4.2 (1H, m), 3.51 and 3.20 (2H, ABq, J=18 Hz), 3.07 (12H, q, J=7 Hz), 2.4–2.1 (2H, m), 1.9–1.4 (4H, m), 2.12 (3H, S), 1.97 (3H, S), 1.29 (18H, t, J=7 Hz)

REFERENCE EXAMPLE 1

(Synthesis of 7-aminocephalosporanic acid)

N,N-Dimethylaniline (44.4 ml) was added to a solution of the ditriethylamine salt of 3-acetoxymethyl-7-(D-5-carboxy-5-phenoxycarbonylaminovaleramido)-3-cephem-4-carboxylic acid as obtained in Example 3 in methylene chloride and the mixture was cooled to −40° C. Then, propionyl chloride (30.4 ml) was added and the whole mixture was stirred at that temperature for 30 minutes. Phosphorus pentachloride (26.0 g) was added and the whole mixture was stirred at that temperature for further 30 minutes. Isobutyl alcohol (200 ml) was added and the resultant mixture was warmed to room temperature (20° C.) and stirred for 30 minutes. Water (200 ml) was then added and stirring was continued for further 30 minutes. Acetone (300 ml) was added to the aqueous layer and the pH of the solution was adjusted to 3.5 by addition of 20% sodium hydroxide aqueous solution. The resultant crystalline precipitate was collected by filtration and dried under reduced pressure to give 10.54 g of 7-aminocephalosporanic acid as a white powder. The yield from 7-(D-5-aminoadipamido)-3-hydroxymethyl-3-cephem-4-carboxylic acid sodium salt was 77.4%.

REFERENCE EXAMPLE 2

(The reaction was carried out in a water-free organic solvent.)

7-(D-5-Carboxy-5-phenoxycarbonylaminovaleramido)-3-hydroxymethyl-3-cephem-4-carboxylic acid ditriethylamine salt (2.04 g), triethylamine (0.82 ml) and 4-(dimethylamino)pyridine (10 mg) were dissolved in acetonitrile (20 ml). Acetic anhydride (0.55 ml) was added dropwise to the solution with ice cooling over 6 minutes. The mixture was then stirred with ice cooling for 20 minutes to complete the reaction. Assay by high-performance liquid chromatography revealed that the starting material 7-(D-5-carboxy-5-phenoxycarbonylaminovaleramido)-3-hydroxymethyl-3-cephem-4-carboxylic acid was not found in the reaction mixture any longer but that said mixture contained 0.811 g (yield 51.7%) of 3-acetoxymethyl-7-(D-5- carboxy-5-phenoxycarbonylaminovaleramido)-3-cephem-4-carboxylic acid and 0.671 g (yield 48.2%) of 7-(D-5-carboxy-5-phenoxycarbonylaminovaleramido)cephalosporanolactone.

What we claim is:

1. A method of producing a 3-alkanoyloxymethyl-3-cephem-4-carboxylic acid which comprises reacting a 3-hydroxymethyl-3-cephem-4-carboxylic acid with a compound of the formula:

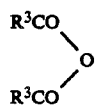

wherein $R^3$ is an alkyl group containing 1 to 8 carbon atoms in an aqueous medium in the presence of a tri-$C_{1-6}$-alkylamino or cyclic tertiary amine and a 4-(tertiary amino)pyridine.

2. A method according to claim 1 for producing a 3-alkanoyloxymethyl-3-cephem-4-carboxylic acid of the formula

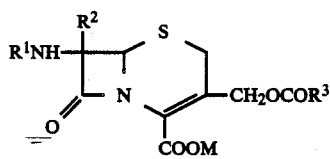

wherein $R^1$ is a hydrogen atom, amino-protective group or an acyl group, $R^2$ is a hydrogen atom, methoxy group or formylamino group, $R^3$ is an alkyl group containing 1 to 8 carbon atoms, and M is a hydrogen atom, alkali metal, alkaline earth metal or ammonium group, which comprises reacting a 3-hydroxymethyl-3-cephem-4-carboxylic acid of the formula

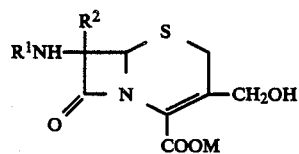

wherein the symbols $R^1$, $R^2$ and M are as defined above, with a compound of the formula

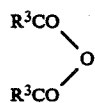

wherein $R^3$ is as defined above in an aqueous medium in the presence of a tri-$C_{1-6}$alkylamine or cyclic tertiary amine and a 4-(tertiary amino)pyridine.

3. A method according to claim 1 for producing a 3-acetoxymethyl-3-cephem-4-carboxylic acid of the formula

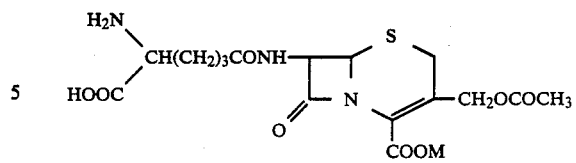

wherein M is a hydrogen atom, alkali metal, alkaline earth metal or ammonium group, and the amino and/or carboxyl group may be protected, which comprises reacting a 3-hydroxymethyl-3-cephem-4-carboxylic acid of the formula

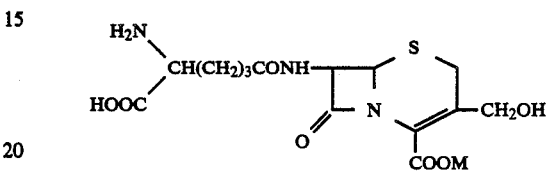

wherein M is as defined above, and the amino and/or carboxyl group may be protected, with acetic anhydride in water in the presence of a tri-$C_{1-6}$alkylamine or cyclic tertiary amine and a 4-(tertiary amino)pyridine.

4. In a method of producing a 3-alkanoloxymethyl-3-cephem-4-carboxylic acid by reacting a 3-hydroxymethyl-3-cephem-4-carboxylic acid with a compound of the formula:

wherein $R^3$ is as defined in claim 1 in a solvent in the presence of a tri-$C_{1-6}$alkylamine or cyclic tertiary amine and a catalyst, the improvement wherein the solvent is an aqueous medium and the catalyst is a 4-(tertiary amino)pyridine.

5. A method according to claim 1, wherein the aqueous medium is water or a mixture of water and an organic solvent.

6. A method according to claim 5, wherein the amount of water in the mixture is 0.01 to 10 volume parts per volume part of the organic solvent, and is 2 to 100 mole per mole of the saturated fatty acid anhydride.

7. A method according to claim 1, wherein the 4(tertiary amino)pyridine is a compound of the formula

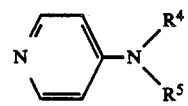

wherein $R^4$ and $R^5$ are the same or different and each is an alkyl group containing 1 to 6 carbon atoms, or $R^4$ and $R^5$ combinedly together with the adjacent nitrogen atom represent a cyclic amino group.

8. A method according to claim 1, wherein the 4-(tertiary amino)pyridine is used in an amount of not more than 0.02 mole per mole of the saturated fatty acid anhydride.

* * * * *